United States Patent
Price et al.

(10) Patent No.: US 9,599,554 B2
(45) Date of Patent: *Mar. 21, 2017

(54) WAVELENGTH-DEPENDENT LIGHT INTENSITY MODULATION IN MULTIVARIATE OPTICAL COMPUTING DEVICES USING POLARIZERS

(71) Applicant: Halliburton Energy Services, Inc., Houston, TX (US)

(72) Inventors: James M. Price, The Woodlands, TX (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 94 days.

This patent is subject to a terminal disclaimer.

(21) Appl. No.: 14/423,382

(22) PCT Filed: Mar. 7, 2014

(86) PCT No.: PCT/US2014/021626
§ 371 (c)(1),
(2) Date: Feb. 23, 2015

(87) PCT Pub. No.: WO2015/134036
PCT Pub. Date: Sep. 11, 2015

(65) Prior Publication Data
US 2016/0252449 A1    Sep. 1, 2016

(51) Int. Cl.
| | | |
|---|---|---|
| *G01J 4/00* | (2006.01) |
| *G01N 21/31* | (2006.01) |
| *G01N 21/21* | (2006.01) |
| *G01N 21/39* | (2006.01) |
| *G01J 3/12* | (2006.01) |
| *G01J 3/42* | (2006.01) |
| *G01J 3/433* | (2006.01) |
| *G01J 3/02* | (2006.01) |

(52) U.S. Cl.
CPC ............ *G01N 21/31* (2013.01); *G01J 3/0224* (2013.01); *G01J 3/12* (2013.01); *G01J 3/42* (2013.01); *G01J 3/433* (2013.01); *G01N 21/21* (2013.01); *G01N 21/39* (2013.01); *G01N 2201/0683* (2013.01)

(58) Field of Classification Search
CPC . G01N 21/21; G01B 11/18; G01J 4/00; G01J 4/04; G01J 4/02
USPC .......................................... 356/366
See application file for complete search history.

(56) References Cited

U.S. PATENT DOCUMENTS

| | | |
|---|---|---|
| 5,482,830 A | 1/1996 | Bogart et al. |
| 6,198,531 B1 | 3/2001 | Myrick et al. |

(Continued)

OTHER PUBLICATIONS

International Search Report and the Written Opinion of the International Searching Authority, or the Declaration, Dec. 4, 2014, PCT/US2014/021626, 11 pages, International Searching Authority, KR.

*Primary Examiner* — Tarifur Chowdhury
*Assistant Examiner* — Md M Rahman
(74) *Attorney, Agent, or Firm* — Haynes and Boone, LLP (57) ABSTRACT

Multivariate optical computing using polarizers to modulate the intensity of sample-interacted light. The polarizer(s), along with other device components, produce a spectroscopic intensity profile that mimics the regression vector that corresponds to the sample characteristic(s) of interest.

46 Claims, 3 Drawing Sheets

(56) References Cited

U.S. PATENT DOCUMENTS

| | | | |
|---|---|---|---|
| 6,529,276 B1 | 3/2003 | Myrick | |
| 2002/0179301 A1* | 12/2002 | Schultz | E21B 47/01 166/250.01 |
| 2003/0197864 A1* | 10/2003 | Wei | G01B 11/065 356/369 |
| 2007/0177240 A1* | 8/2007 | Van Beek | A61B 5/14532 359/196.1 |
| 2010/0265509 A1 | 10/2010 | Jones et al. | |
| 2011/0051143 A1* | 3/2011 | Flanders | G01B 9/02004 356/451 |
| 2012/0211650 A1 | 8/2012 | Jones et al. | |
| 2013/0034842 A1 | 2/2013 | Tunheim et al. | |
| 2013/0284894 A1 | 10/2013 | Freese et al. | |
| 2015/0002852 A1* | 1/2015 | de Groot | G01B 9/0209 356/491 |
| 2015/0276582 A1* | 10/2015 | Skinner | G01N 21/314 356/365 |

\* cited by examiner

WAVELENGTH-DEPENDENT LIGHT INTENSITY MODULATION IN MULTIVARIATE OPTICAL COMPUTING DEVICES USING POLARIZERS

The present application is a U.S. National Stage patent application of International Patent Application No. PCT/US2014/021626, filed on Mar. 7, 2014, the benefit of which is claimed and the disclosure of which is incorporated herein by reference in its entirety.

FIELD OF THE DISCLOSURE

The present disclosure relates generally to optical sensors and, more specifically, to multivariate optical computing systems wherein polarizers are used to modulate the intensity of sample-interacted light to thereby determine sample characteristics.

BACKGROUND

In recent years, optical computing devices have been developed for chemical sensing applications including, but not limited to, those in the oil and gas industry in the form of optical sensors on downhole or surface equipment to evaluate a variety of reservoir fluid properties. In general, an optical computing device is a device configured to receive an input of electromagnetic radiation from a sample and produce an output of electromagnetic radiation from a processing element, wherein measured integrated intensity of the electromagnetic radiation from the processing element is related to a component or components within the sample. The optical computing device may be, for example, an Integrated Computational Element ("ICE"). One type of an ICE is a multi-layered optical thin film optical interference device, also known as a multivariate optical element ("MOE").

Fundamentally, optical computing devices utilize optical elements to perform calculations, as opposed to the hard-wired circuits of conventional electronic processors. When light from a light source interacts with a substance, unique physical and chemical information about the substance is encoded in the electromagnetic radiation that is reflected from, transmitted through, or radiated from the sample. Thus, the optical computing device, for example through use of the ICE and one or more detectors, is capable of extracting the information of one or multiple characteristics/analytes within a substance and converting that information into a detectable output signal reflecting the overall properties of a sample. Such characteristics may include, for example, the presence of certain elements, compositions, fluid phases, etc. existing within the substance.

Traditional ICEs include pluralities of optical thin film layers consisting of various materials whose complex indices of refraction and size (e.g., thickness) varies between each layer. A traditional ICE design refers to the substrate, number and thicknesses of the respective layers of the traditional ICE, and the refractive indices of the substrate and layers. The layers may be strategically deposited and sized so as to selectively pass predetermined fractions of electromagnetic radiation at different wavelengths configured to substantially mimic a regression vector corresponding to a particular physical or chemical characteristic of interest of a substance of interest. Accordingly, a traditional ICE design will exhibit a transmission function that is weighted with respect to wavelength. As a result, the output light intensity from the ICE conveyed to the detector may be related to the physical or chemical characteristic of interest for the substance.

Currently, ICE designs are assessed by applying an ICE regression vector to a single set of calibration data (i.e., spectral data set) to evaluate a performance factor, for example but not limited to, a standard error of calibration ("SEC"). This procedure is performed on a set of spectral data that describes a single chemical system that contains one or more components: its target characteristic and the remaining components (including spectral interferents), usually referred to the matrix. A subset of the chemical system can be used for validation purposes to calculate the performance factor, for example, the standard error of prediction; and represents the same chemical system as the calibration set. An illustrative ICE can be constructed as a series of alternating layers of high and low refractive index materials with associated thicknesses deposited onto an optical substrate. Such a device has an optical transmission function (T), designed by assessing a performance factor (e.g. SEC) and using a minimization function to adjust the layer thicknesses to design an ICE with an optimal performance factor (e.g. low SEC), which is thus as predictive as possible. As a result, the design and fabrication of multi-layered thin film ICEs can be very time-consuming and costly.

Accordingly, there is a need in the art for a more cost-effective approach to multivariate optical computing.

DESCRIPTION OF ILLUSTRATIVE EMBODIMENTS

Illustrative embodiments and related methodologies of the present disclosure are described below as they might be employed in an optical computing device wherein, in contrast to traditional ICE, polarizers are used to modulate the intensity of sample-interacted light to thereby determine one or more sample characteristics. In the interest of clarity, not all features of an actual implementation or methodology are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methodologies of the disclosure will become apparent from consideration of the following description and drawings.

Illustrative embodiments and related methods of the present disclosure are directed to an intensity-dependent optical computing device and method for performing multivariate optical computing using polarizers. The embodiments taught herein provide an alternative approach to traditional optical computing by replacing the multilayer thin film device (e.g., ICE) with one or more polarizers in order to produce the spectroscopic intensity profile that mimics a regression vector that weights the orthogonal component(s) corresponding to the sample characteristic(s) of interest. During operation, sample-interacted light, having a given light intensity and wavelength, is processed through one or more polarizers that modulate the intensity of the sample-interacted light to thereby produce polarized light. The level of intensity modulation is selected to mimic the regression vector that corresponds to a particular physical or chemical characteristic of interest present in a sample. The level of intensity modulation, and thus the regression vector, may be altered by manipulating the angular orientation of the polarizer(s) to allow the detection of multiple sample characteristics. Ultimately, the polarized light is received by a detector which produces an output signal utilized by a processor to determine the sample characteristic(s).

As used herein, the term "substance," "sample" or variations thereof, refers to at least a portion of matter or material of interest to be tested or otherwise evaluated with the help of the optical computing devices described herein. The substance may be any fluid capable of flowing, including particulate solids, liquids, gases (e.g., air, nitrogen, carbon dioxide, argon, helium, methane, ethane, butane, and other hydrocarbon gases, hydrogen sulfide, and combinations thereof), slurries, emulsions, powders (e.g., cements, concretes, etc.), drilling fluids (i.e., "muds"), glasses, mixtures, combinations thereof. The substance may include, but is not limited to, aqueous fluids (e.g., water, brines, etc.), non-aqueous fluids (e.g., organic compounds, hydrocarbons, oil, a refined component of oil, petrochemical products, and the like), acids, surfactants, biocides, bleaches, corrosion inhibitors, foamers and foaming agents, breakers, scavengers, stabilizers, clarifiers, detergents, treatment fluids, fracturing fluids, formation fluids, or any oilfield fluid, chemical, or substance commonly found in the oil and gas industry. The substance may also refer to solid materials such as, but not limited to, rock formations, concrete, solid wellbore surfaces, pipes or flow lines, and solid surfaces of any wellbore tool or projectile (e.g., balls, darts, plugs, etc.).

As used herein, the term "characteristic" or "characteristic of interest" refers to a chemical, mechanical, or physical property of a substance or a sample of the substance. The characteristic of the substance may include a quantitative or qualitative value of one or more chemical constituents or compounds present therein or any physical property associated therewith. Such chemical constituents and compounds may be referred to herein as "analytes." Illustrative characteristics of a substance that can be analyzed with the help of the optical processing elements described herein can include, for example, chemical composition (e.g., identity and concentration in total or of individual components), ratios of compositions within the sample, phase presence (e.g., gas, oil, water, etc.), impurity content, pH, alkalinity, viscosity, density, ionic strength, total dissolved solids, salt content (e.g., salinity), porosity, opacity, bacteria content, total hardness, transmittance, state of matter (solid, liquid, gas, emulsion, mixtures thereof, etc.), and the like.

As used herein, the term "electromagnetic radiation" refers to radio waves, microwave radiation, terahertz, infrared and near-infrared radiation, visible light, fluorescent light, ultraviolet light, X-ray radiation and gamma ray radiation.

As used herein, the phrase "optically interact" or variations thereof refers to the reflection, transmission, scattering, diffraction, or absorption of electromagnetic radiation either on, through, or from an optical processing element (e.g., an ICE) or a substance being analyzed with the optical computing device. Accordingly, optically interacted light refers to electromagnetic radiation that has been reflected, transmitted, scattered, diffracted, or absorbed by, emitted, or re-radiated, for example, using an optical processing element, but may also apply to optical interaction with a substance.

As used herein, the term "optical computing device" refers to an optical device that is configured to receive an input of electromagnetic radiation associated with a substance and produce an output of electromagnetic radiation from an optical processing element arranged within or otherwise associated with the optical computing device. The optical processing element may be, for example, an ICE. The electromagnetic radiation that optically interacts with the optical processing element is changed so as to be readable by a detector, such that an output of the detector can be correlated to a particular characteristic of the substance being analyzed. The output of electromagnetic radiation from the optical processing element can be reflected, transmitted, and/or dispersed electromagnetic radiation. Whether the detector analyzes reflected, transmitted, or dispersed electromagnetic radiation may be dictated by the structural parameters of the optical computing device as well as other considerations known to those skilled in the art.

As used herein, the terms "modulate" and variations thereof refer to the changing of one light intensity to another.

Figure 1:
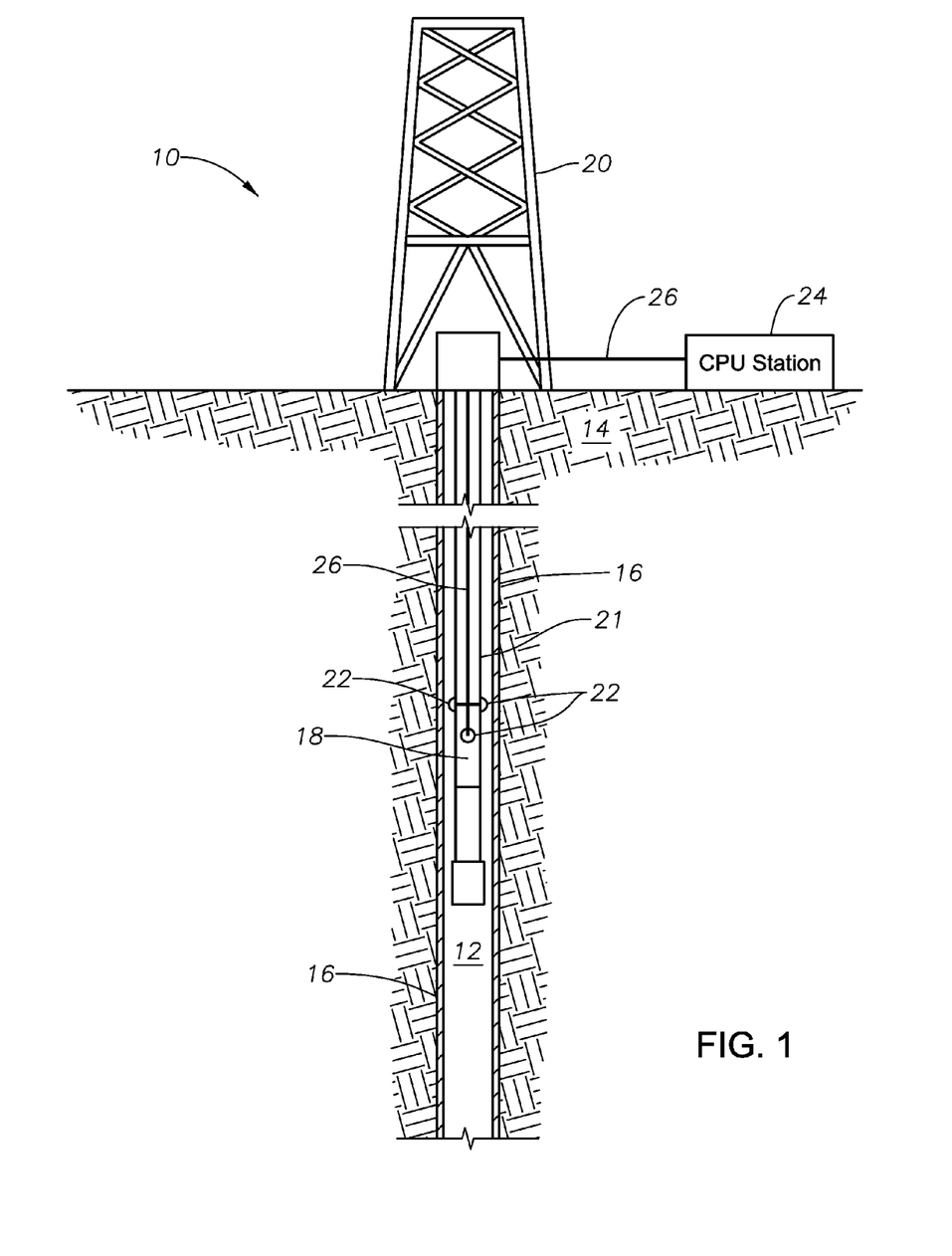
FIG. 1 illustrates a well system having optical computing devices deployed therein for sample characteristic detection according to certain illustrative embodiments of the present disclosure.

Although the optical computing devices described herein may be utilized in a variety of environments, the following description will focus on downhole well applications (e.g., a downhole reservoir interrogation system). FIG. 1 illustrates a plurality of optical computing devices 22 positioned along a workstring 21 extending along a downhole well system 10 according to certain illustrative embodiments of the present disclosure. Workstring 21 may be, for example, a wireline assembly, logging-while-drilling assembly, measuring-while drilling assembly, production string or other drilling assembly. Well system 10 comprises a vertical wellbore 12 extending down into a hydrocarbon reservoir 14 (although not illustrated, wellbore 12 may also comprise one or more lateral sections). Wellbore equipment 20 is positioned atop vertical wellbore 12, as understood in the art. Wellbore equipment may be, for example, a blow out preventer, derrick, floating platform, etc. As understood in the art, after vertical wellbore 12 is formed, tubulars 16 (casing, for example) are extended therein to complete wellbore 12.

One or more optical computing devices 22 may be positioned along wellbore 12 at any desired location. In certain embodiments, optical computing devices 22 are positioned along the internal or external surfaces of downhole tool 18 (as shown in FIG. 1) which may be, for example, intervention equipment, surveying equipment, or completion equipment including valves, packers, screens, mandrels, gauge mandrels, in addition to casing or tubing tubulars/joints as referenced below. Alternatively, however, optical computing devices 22 may be permanently or removably attached to tubulars 16 and distributed throughout wellbore 12 in any area in which sample characteristic detection/monitoring is desired. Optical computing devices 22 may be coupled to a remote power supply (located on the surface or a power generator positioned downhole along the wellbore, for example), while in other embodiments each optical computing device 22 comprises an on-board battery. Moreover, optical computing devices 22 are communicably coupled to a CPU station 24 via a communications link 26, such as, for example, a wireline or other suitable communications link. Those ordinarily skilled in the art having the benefit of this disclosure will readily appreciate that the number and location of optical computing devices 22 may be manipulated as desired.

Optical computing devices 22 comprise an ICE that optically interacts with a sample of interest (wellbore fluid, downhole tool component, tubular, for example) to determine the sample characteristic. More specifically, the ICE utilized in embodiments of the present disclosure is one or more polarizers. Illustrative characteristics include the presence and quantity of specific inorganic gases such as, for example, $CO_2$ and $H_2S$, hydrocarbon gases and liquids such as methane (C1), ethane (C2) propane (C3), butane (C4), and pentane (C5), saline water, dissolved ions (Ba, Cl, Na, Fe, or Sr, for example), or various other characteristics (pH., density and specific gravity, viscosity, total dissolved solids, sand content, gas-to-oil ratio (GOR), phase etc.). In certain embodiments, a single optical computing device 22 may detect a single characteristic, while in others a single optical computing device 22 may determine multiple characteristics, as will be understood by those ordinarily skilled in the art having the benefit of this disclosure.

CPU station 24 comprises a signal processor (not shown), communications module (not shown) and other circuitry necessary to achieve the objectives of the present disclosure, as will be understood by those ordinarily skilled in the art having the benefit of this disclosure. In addition, it will also be recognized that the software instructions necessary to carry out the objectives of the present disclosure may be stored within storage located in CPU station 24 or loaded into that storage from a CD-ROM or other appropriate storage media via wired or wireless methods. Communications link 26 provides a medium of communication between CPU station 24 and optical computing devices 22. Communications link 26 may be a wired link, such as, for example, a wireline or fiber optic cable extending down into vertical wellbore 12. Alternatively, however, communications link 26 may be a wireless link, such as, for example, an electromagnetic device of suitable frequency, or other methods including acoustic communication and like devices.

In certain illustrative embodiments, CPU station 24, via its signal processor, controls operation of each optical computing device 22. In addition to sensing operations, CPU station 24 may also control activation and deactivation of optical computing devices 22. Optical computing devices 22 each include a transmitter and receiver (transceiver, for example) (not shown) that allows bi-directional communication over communications link 26 in real-time. In certain illustrative embodiments, optical computing devices 22 will transmit all or a portion of the sample characteristic data to CPU station 24 for further analysis. However, in other embodiments, such analysis is completely handled by each optical computing device 22 and the resulting data is then transmitted to CPU station 24 for storage or subsequent analysis. In either embodiment, the processor handling the computations analyzes the characteristic data and, through utilization of Equation of State ("EOS") or other optical analysis techniques, derives the characteristic indicated by the transmitted data, as will be readily understood by those ordinarily skilled in the art having the benefit of this disclosure.

Figure 2:
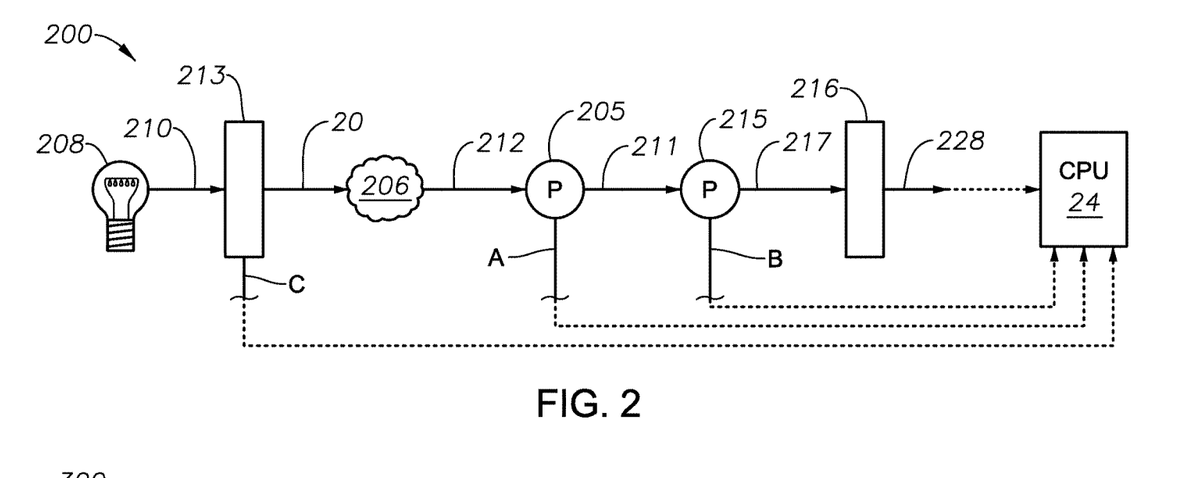
FIG. 2 is a block diagram of an optical computing device that utilizes two polarizers, according to certain illustrative embodiments of the present disclosure.

FIG. 2 is a block diagram of an optical computing device 200 that utilizes two polarizers, according to certain illustrative embodiments of the present disclosure. An electromagnetic radiation source 208 may be configured to emit or otherwise generate electromagnetic radiation 210. As understood in the art, electromagnetic radiation source 208 may be any device capable of emitting or generating electromagnetic radiation with a source spectrum over a particular wavelength range. In some implementations, the source spectrum can have non-zero intensity over the entire or most of the particular wavelength range. In some implementations, the source spectrum extends through UV-vis (0.2-0.8 µm) and near-IR (0.8-2.5 µm) spectral ranges. Alternatively, or additionally, the source spectrum extends through an IR (2.5-100 µm) spectral range. In some implementations, the light source 208 is tunable and is configured in combination with time resolved signal detection and processing. For example, electromagnetic radiation source 208 may be a light bulb, light emitting device, laser, blackbody, photonic crystal, or X-Ray source, etc.

As shown in FIG. 2, electromagnetic radiation 210 is directed to wavelength scanner 213 to produce a single desired wavelength λ of electromagnetic radiation 210 having maximum intensity. Wavelength scanner 213 may be, for example, a monochromator or grating. Thereafter, electromagnetic radiation 210 optically interacts with sample 206 (wellbore fluid flowing through wellbores 12, for example) to thereby generate sample-interacted light 212. After being illuminated with electromagnetic radiation 210, sample 206 containing an analyte of interest (a characteristic of the sample, for example) produces an output of electromagnetic radiation (sample-interacted light 212) which contains spectral information that corresponds to the sample characteristics. Sample 206 may be any fluid (liquid or gas), solid substance or material such as, for example, downhole fluids, rock formations, slurries, sands, muds, drill cuttings, concrete, other solid surfaces, etc. In this specific embodiment, however, sample 206 is a multiphase wellbore fluid (comprising oil, gas, water, solids, for example) consisting of a variety of fluid characteristics such as, for example, C1-C4 and higher hydrocarbons, groupings of such elements, and saline water.

Sample 206 may be provided to optical computing device 200 through a flow pipe or sample cell, for example, containing sample 206, whereby it is introduced to electromagnetic radiation 210. Alternatively, optical computing device 200 may utilize an optical configuration consisting of an internal reflectance element which analyzes the wellbore fluid as it flows thereby. While FIG. 2 shows electromagnetic radiation 210 as passing through or incident upon the sample 206 to produce sample-interacted light 212 (i.e., transmission or fluorescent mode), it is also contemplated herein to reflect electromagnetic radiation 210 off of the sample 206 (i.e., reflectance mode), such as in the case of a sample 206 that is translucent, opaque, or solid, and equally generate the sample-interacted light 212.

Sample-interacted light 212 then optically interacts with a first polarizer 205. As will be understood by those ordinarily skilled in the art having the benefit of this disclosure, a polarizer is an optical element that only transmits a certain amount of light dependent upon its polarization state, while blocking light at other polarizations. Examples may include one or more polarizers such as, for example, absorptive polarizers, beam splitting polarizers, circular polarizers, or photo-elastic modulators. Therefore, once interacted with first polarizer 205, sample-interacted light 212 becomes polarized to thereby produce first polarized light 211. Here, first polarizer 205 only allows a preferred electric field orientation to be transmitted through it, thereby defining a given orientation (P, S or some intermediate P&S) and phase. Thus, first polarizer 205 defines the polarization state (i.e., first polarization state) of sample-interacted light 212. As will be discussed below, first polarizer 205 is coupled to CPU station 24 (or an on-board processor) via bi-directional link A, whereby CPU station 24 sends a signal to first polarizer 205 to thereby define the first polarization state by manipulating the angular orientation of polarizer 205.

First polarized light 211 is then conveyed to second polarizer 215 where it optically interacts to produce second polarized light 217. As with first polarizer 205, second polarizer 215 only allows a defined amount of light to transmit through dependent upon its polarization setting (i.e., angular orientation). Here, second polarizer 215 defines a second polarization state of first polarized light 211 to produce a second polarized light 217, or that represents a change in polarization between first and second polarized lights 211,217. This polarization change also results in a change of light intensity, thus resulting in a modulation of the light intensity of sample-interacted light 212. The change in polarization, or more specifically the angle, between the first and second polarizers 205,215 is selected such that their combined wavelength dependent spectroscopic intensity profile matches a regression vector that weights at least one orthogonal component of sample-interacted light 212, thus producing the intensity profile needed to determine the sample characteristic of interest. Alternatively, however, in certain instances first polarizer 205 may be sufficient to provide the desired intensity and, thus, second polarizer 215 would maintain the same polarization/intensity. Therefore, in certain embodiments, second polarized light 217 may represent a change in polarization between the first and second polarized lights 211,217, while in other embodiments second polarized light 217 has the same polarization (and, thus, intensity) of first polarized light 211.

Nevertheless, second polarized light 217 is then directed to detector 216 for analysis and quantification. Here, detector 216 converts the intensity of second polarized light 217 into an electronic signal 228 that is used by CPU station 24 to determine the sample characteristic of interest, as will be understood by those ordinarily skilled in the art having the benefit of this disclosure.

Detector 216 may be any device capable of detecting electromagnetic radiation, and may be generally characterized as an optical transducer. For example, detector 216 may be, but is not limited to, a thermal detector such as a thermopile or photoacoustic detector, a semiconductor detector, a piezo-electric detector, charge coupled device detector, video or array detector, split detector, photon detector (such as a photomultiplier tube), photodiodes, and/or combinations thereof, or the like, or other detectors known to those ordinarily skilled in the art. Detector 216 is further configured to produce the output signal 228 in the form of a voltage or current that corresponds to the wavelength dependent intensity of second polarized light 217. In at least one embodiment, a wavelength dependent output signal 228 produced by detector 216, is stored and processed by CPU 24. Thus, the processed signal relates to the concentration of the characteristic of the sample 206 and may be directly proportional. In other embodiments, the relationship may be a polynomial function, an exponential function, and/or a logarithmic function.

In certain illustrative embodiments, the angular orientations of first and second polarizers 205,215 may be manipulated to thereby alter the level of intensity modulation, thus allowing the detection of multiple sample characteristics. To achieve this, first and second polarizers 205,215 may be operationally coupled to an actuation device (not shown) to rotate the polarizers as desired. As shown in FIG. 2, CPU station 24 is coupled to polarizers 205,215 (and their actuation devices), via links A and B to thereby receive data reflecting the first and second polarization states and to allow CPU station 24 to control the angular orientations of the first and second polarizers 205,215, and therefore the detected sample characteristic of interest. In addition, CPU station 24 is also operationally coupled to wavelength scanner 213 via link C to thereby control the wavelength of electromagnetic radiation 210. For example, the wavelength and intensity of electromagnetic radiation 210 may be selected by CPU station 24 and controlled via link C, whereby the angular orientations of polarizers 205,215 may be adjusted accordingly in order to span the wavelength spectrum of interest. In doing so, CPU station 24 controls the angle between first and second polarizers 205,215 to thereby modulate the light intensity as desired for a given wavelength. Thus, through links A,B,C, CPU station 24 may systematically tune optical computing device 200 to the desired wavelength and polarizer angle, such that the intensity of second polarized light 217 mimics the desired regression vector. As a result, output signal 228 will be a function of the wavelength of light and angles of first and second polarizers 205,215. CPU station 24 then analyzes the wavelength dependent intensity of output signal 228 to determine the characteristics of interest.

A more detailed description of illustrative computations used by CPU station 24 to determine the sample characteristic will now be described. As previously described, the illustrative embodiments of the present disclosure utilize one or more polarizers and a wavelength scanner to mimic the desired regression vector. Although illustrated in FIG. 2 as having first and second polarizers 205,215 after sample 206, alternative embodiments may position first and second polarizers 205,215 before sample 206, as will be understood by those ordinarily skilled in the art having the benefit of this disclosure. Nevertheless, the amount of light transmitted through a polarizer will depend on the polarizer angle θ, i.e. the angle between the incidence beam's polarization state and the axis of the polarizer. Thus, the light intensity I can be represented as:

$$I = I_0 \cos^2 \theta \qquad \text{Eq.(1)}.$$

If, for example, the incident beam is un-polarized, then the transmitted intensity will be equal to ½ the incident light since the average value of $\cos^2 \theta$ is ½; thus, the use of two polarizers is utilized in one illustrative embodiment of the present disclosure.

Through links A,B, as described above, the angular orientations of first and second polarizers 205,215 may be altered such that the light intensity is modulated as desired. Wavelength scanner 213 and first/second polarizers 205,215 are communicably coupled to CPU station 24 (and each other) via links A,B,C, such that CPU station 24 may systematically tune to the desired wavelength and polarizer angle, respectively. As a result, the combined spectroscopic intensity profile of polarizers 205,215 matches the desired regression vector that weighs the orthogonal component(s) corresponding to the sample characteristics of interest for a given wavelength.

By properly selecting the angular orientations of first and second polarizers 205,215, optical computing device 200 may be configured to selectively pass/reflect/refract predetermined fractions of electromagnetic radiation at different wavelengths. Each wavelength is given a predetermined weighting or loading factor. The angular orientations, and thus the spectroscopic intensity profiles of the polarizers may be determined using a variety of approximation methods from the spectrum of the characteristic or analyte of interest. These methods may include inverse Fourier transform ("IFT") of the optical transmission spectrum and configuring the polarizer angle difference as the physical representation of the IFT.

The weightings that the polarizers apply at each wavelength may be set to the regression weightings described with respect to a known equation, data, or spectral signature. When electromagnetic radiation interacts with a substance, unique physical and chemical information about the substance may be encoded in the electromagnetic radiation that is reflected from, transmitted through, or radiated from the substance. This information is often referred to as the spectral "fingerprint" of the substance. The polarizers may be configured to perform the dot product of the received electromagnetic radiation and the combined wavelength dependent transmission function of the polarizers. The combined wavelength dependent transmission function (i.e., spectroscopic intensity profile) of the polarizers is dependent on the wavelength dependent angular orientation of the polarizers. The combined spectroscopic intensity profile is then analogous to a desired regression vector derived from the solution to a multivariate analysis problem targeting a specific component of the substance being analyzed. As a result, the wavelength dependent intensity of the second polarized light 217 is related to (e.g., directly proportional to) the characteristic or analyte of interest of the sample 206.

With reference to Equation 1 above, to further illustrate the theory applied in the present disclosure, consider a polarizer as a filter which only allows light of a given polarization state to be transmitted, while suppressing light of all other polarization states. If an un-polarized light (light with a random distribution of all polarizations) is being supplied as electromagnetic radiation 210 with an intensity of 1 mW, and is conveyed as sample-interacted light 212 through first polarizer 205 which is fixed to P polarization, then it will only allow the P Polarized light to be transmitted as first polarized light 211, while suppressing all S—and S/P combinations; resulting in an intensity of 0.5 mW after first polarizer 205. If the angular orientation of second polarizer 215 is also fixed to the P polarization state, then all of first polarized light 211 will be transmitted since it is already P polarized from first polarizer 205. However, if the second polarizer 215 is fixed to S polarization, no light will be transmitted through as second polarized light 217 since first polarizer 205 had already suppressed all S Polarized light. Considering this, in the illustrative embodiments described herein, the preceding example is generalized by adjusting the angle between the two polarizers in order to get the desired light intensity needed for a given wavelength.

The angular orientations of the first and/or second polarizers 205,215 may be altered in a variety of ways. The amount of light transmitted through the first or second polarizers 205,215 will depend on the angle, i.e., orientation relative to the electric field vector coming from incidence light. In certain embodiments, the azimuthal angle of first polarizer 205 is fixed, while in others the azimuthal angle of first polarizer 205 may be rotating. In such embodiments, the first and second polarizers 205,215 may be operatively coupled to an actuation device (not shown) which rotates the polarizers to a desired angle. Mechanical or electrical rotational motors may be utilized as the actuation devices, in addition to a linear actuator in which linear motion is converted into rotational motion.

The angles of rotation may result in, for example, a pure P polarized light, pure S polarized light or an intermediate P and S polarized light. Alternatively, the actuation device may continuously rotate where not one defined polarized state is generated, but all of them over the course of one full rotation; for example, starting with pure P, then intermediate P and S, and then pure S polarized light. In other examples, the first polarizer 205 may be operatively coupled to the actuation device while second polarizer 215 is stationary. In other examples, first polarizer 205 may be fixed, while second polarizer 215 is coupled to the actuation device and, thus, rotates. As previously mentioned, the angular orientations of first and second polarizers 205,215, along with the wavelength being analyzed, may be communicated to CPU station 24 via links A,B,C to thereby determine the sample characteristic of interest.

Figure 3:
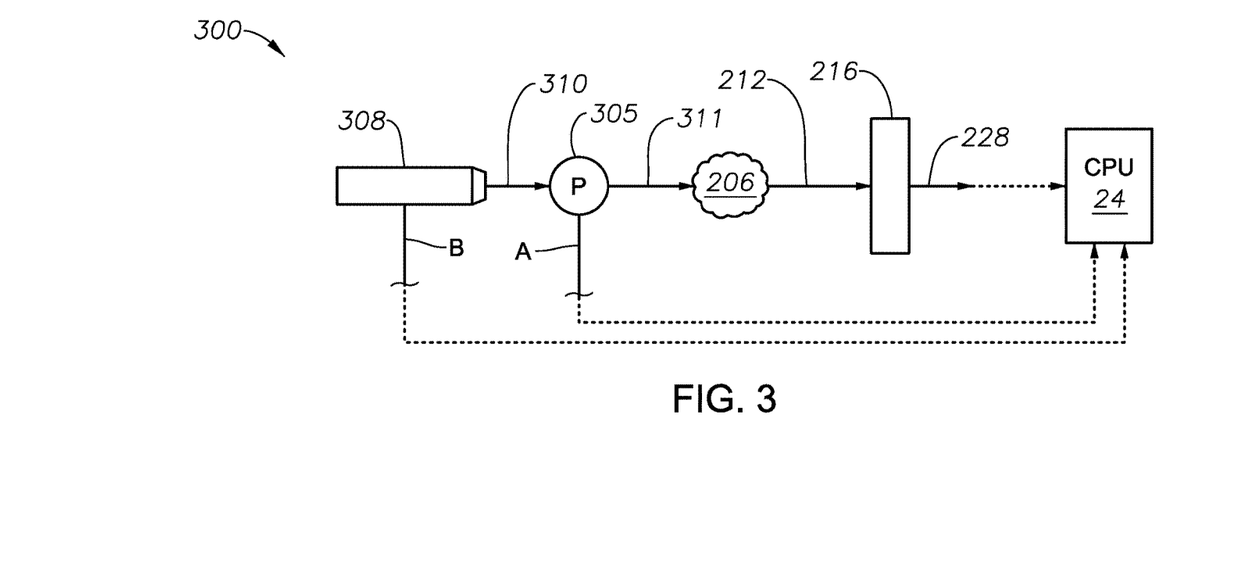
FIG. 3 illustrates a block diagram of yet another optical computing device employing a tunable laser and polarizer, according to certain illustrative embodiments of the present disclosure.

FIG. 3 illustrates a block diagram of yet another optical computing device 300 employing a tunable laser and polarizer, according to certain illustrative embodiments of the present disclosure. Optical computing device 300 is somewhat similar to optical computing device 200 described with reference to FIG. 2 and, therefore, may be best understood with reference thereto, where like numerals indicate like elements. In contrast to optical computing device 200, device 300 includes a tunable laser 308 and a single polarizer 305 to thereby generate polarized light 311. Tunable laser 308 emits electromagnetic radiation 310 having a defined intensity, wavelength and polarization (i.e., first polarization state). Thus, tunable laser 308 serves to replace source 208, wavelength scanner 213 and first polarizer 205 of FIG. 2. Polarizer 305, having a desired angular orientation, is positioned to optically interact with electromagnetic radiation 310 to produce polarized light 311 having a second polarization state different from that the first polarized state of electromagnetic radiation 310. Polarized light 311 then optically interacts with sample 206 to produce sample-interacted light 212. Sample-interacted light 212 is then conveyed to detector 216, whereby output signal 228 is produce whose light intensity corresponds to a desired sample characteristic.

In the example of FIG. 3, the combined spectroscopic intensity profile of tunable laser 308 and polarizer 305 mimics a regression vector that weighs at least one orthogonal component of sample-interacted light 212 which corresponds to the sample characteristic of interest. Tunable laser 308 and polarizer 305 are coupled to CPU station 24 via links B,A, respectively, to thereby allow systematic tuning to a desired wavelength and angular orientation necessary to mimic the regression vector. As previously described, the angular orientation of polarizer 305 may be altered to effect the intensity modulation between the first and second polarization states, thus resulting in the second polarization state that is detected and used to determine the sample characteristic of interest.

For embodiments described in FIGS. 2 and 3, there are at least two illustrative ways the process can be implemented to detect multiple analytes/characteristics. In a first method, the process is the same as for a single characteristic where the wavelength is tuned (via links A,B,C, as described) for a given polarization angle. Then, once that characteristic has been measured (i.e., completed tuning over spectrum of interest), the method involves going back and scanning the wavelength/polarization for the next characteristic of interest. In a second method, the wavelength may be fixed and then a different polarization angle may be scanned for different characteristics of interest. Each of those intensities would be "stored/binned" in memory of CPU 24. Thereafter, CPU 24, via links A,B,C would move onto the next wavelength and scan the polarizer(s) again, and so on. Ultimately, the intensities for each characteristic would be integrated in the detector for each "stored/binned" characteristic.

Figure 4:
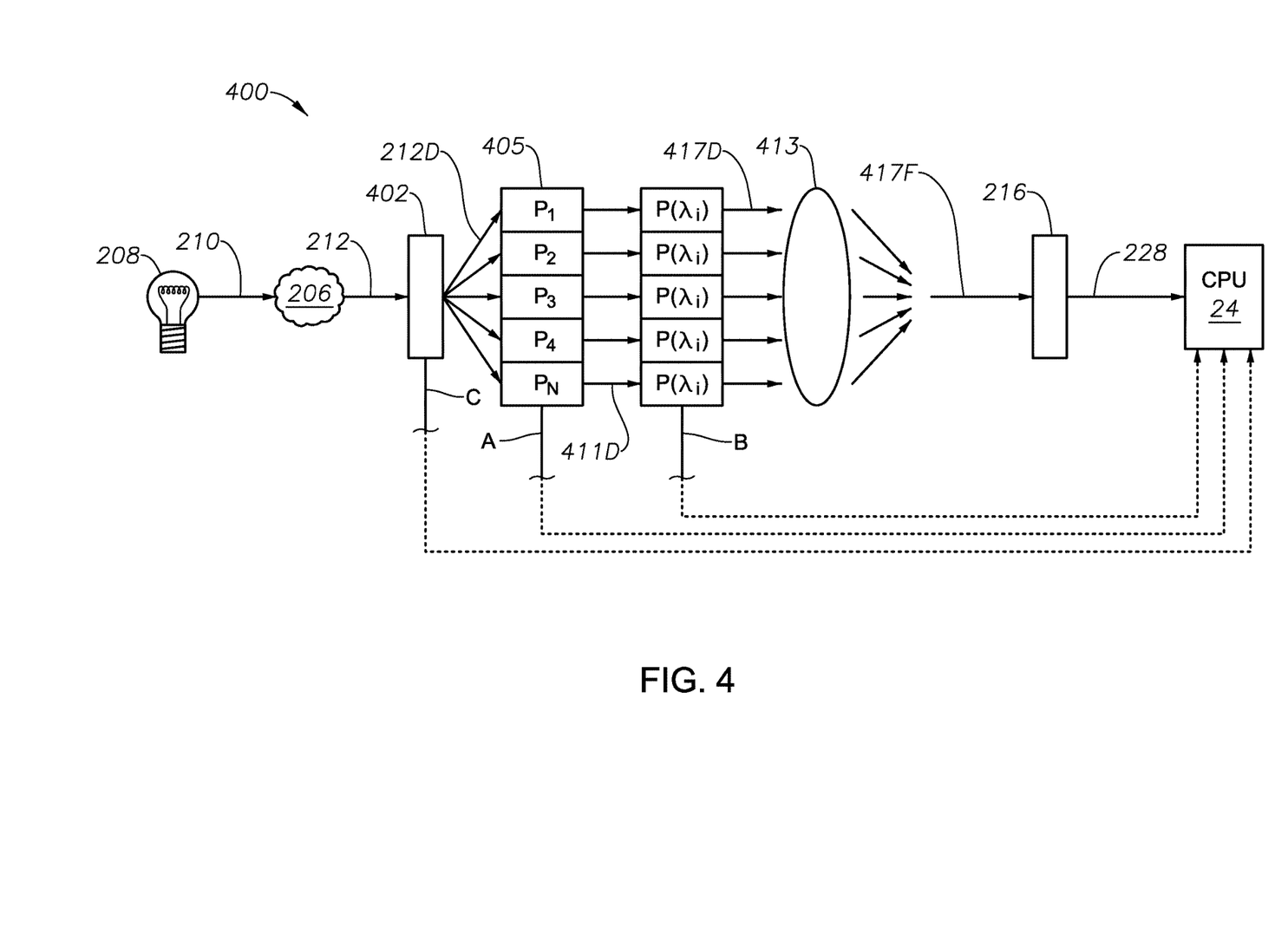
FIG. 4 illustrates a block diagram of yet another optical computing device employing polarizer arrays, according to certain illustrative embodiments of the present disclosure.

FIG. 4 illustrates a block diagram of yet another optical computing device 400 employing polarizer arrays, according to certain illustrative embodiments of the present disclosure. Optical computing device 400 is somewhat similar to optical computing devices 200 and 300 described with reference to FIGS. 2 and 3 and, therefore, may be best understood with reference thereto, where like numerals indicate like elements. In contrast to optical computing devices 200 and 300, device 400 includes a wavelength dispersive element 402, first polarizer array 405, and second polarizer array 415—which eliminate the need for the wavelength scanner of previous embodiments described above. Wavelength dispersive element 402 may be, for example, a grating or prism.

During operation, electromagnetic radiation source 208 generates broadband electromagnetic radiation 210 that optically interacts with sample 206 to produce sample-interacted light 212. Sample-interacted light 212 optically interacts with wavelength dispersive element 402 to produce a broadband wavelength spectrum of dispersed sample-interacted light 212D across first polarizer array 405. Sample-interacted light 212D optically interacts with first polarizer array 405 to produce dispersed first polarized light 411D, which (as previously described) has a first polarization state. Second polarizer array 415 is positioned to optically interact with dispersed first polarized light 411D to produce dispersed second polarized light 417D, which has a second polarization state as previously described. Here, as previously described, first and second polarizer arrays 405, 415 act to modulate the intensity of sample-interacted light 212D. Nevertheless, each polarizer in first polarizer array 405 has a corresponding polarizer in second polarizer array 415, thus forming a plurality of pairs. Second polarizer array 415 includes a plurality of polarizers which are set to a defined polarization for each different wavelength $\lambda_i$, thus spanning the entire spectrum of sample interacted light 212D. Dispersed second polarized light 417D the optically interacts with a lens 413 to focus the light back down to detector 216 where the intensity of focused second polarized light 417F is integrated at all different wavelengths. Detector 216 then outputs signal which is ultimately utilized by CPU 24 (e.g., signal processor) to determined one or more characteristics of sample 206 in real-time.

In certain embodiments, each pair of polarizers comprises different angular orientations. For example, each polarizer in first polarizer array 405 may have a fixed polarization (different or same polarizations), while each polarizer in the second polarizer array 415 may be set to a given polarization for each different wavelength. Moreover, the wavelength spectrums and angular orientations of first and second arrays 405,415 may be manipulated as desired by CPU 24 via links A,B,C. As a result, optical computing device 400 may detect multiple characteristics.

Those ordinarily skilled in the art having the benefit of this disclosure realize the aforementioned optical computing devices are illustrative in nature, and that there are a variety of other optical configurations which may be utilized. These optical configurations not only include the reflection, absorption or transmission methods described herein, but can also involve scattering (Raleigh & Raman, for example) as well as emission (fluorescence, X-ray excitation, etc., for example). In addition, the optical computing devices may comprise a parallel processing configuration whereby the sample-interacted light is split into multiple beams. The multiple beams may then simultaneously go through corresponding polarizers, whereby multiple characteristics of interest are simultaneously detected. The parallel processing configuration is particularly useful in those applications that require extremely low power or no moving parts. Moreover, one or more features of the embodiments described herein, may be combined as desired. Those ordinarily skilled in the art having the benefit of this disclosure will realize the choice of a specific optical configuration is mainly dependent upon the specific application and characteristics of interest.

In addition to downhole or completion applications, the optical computing devices described herein may be utilized in a variety of others environments. Such environments may include, for example, those as diverse as those associated with surface and undersea monitoring, satellite or drone surveillance, pipeline monitoring, or even sensors transiting a body cavity such as a digestive tract. Within those environments, the optical computing devices may be utilized to detect sample characteristics in real-time.

Accordingly, embodiments and related methodologies of the present disclosure provide a number of advantages. First, for example, embodiments disclosed herein eliminate the need for designing and fabricating multi-layered thin film ICEs. Second, embodiments described herein allow multiple characteristics of interest to be analyzed using a single system, rather having multiple thin film ICEs.

Embodiments described herein further relate to any one or more of the following paragraphs:

1. An optical computing device to determine a characteristic of a sample, the optical computing device comprising electromagnetic radiation that optically interacts with a sample to produce sample-interacted light; a first polarizer positioned to optically interact with the sample-interacted light to produce first polarized light; a second polarizer positioned to optically interact with the first polarized light to produce second polarized light; and a detector positioned to measure the second polarized light and thereby generate a signal utilized to determine a characteristic of the sample.

2. An optical computing device as defined in paragraph 1, wherein a combined spectroscopic intensity profile of the first and second polarizers weights at least one orthogonal component of the sample-interacted light, the at least one orthogonal component corresponding to the characteristic of the sample.

3. An optical computing device as defined in paragraphs 1 or 2, further comprising: a broadband light source that produces the electromagnetic radiation; and a wavelength scanner positioned to optically interact with the electromagnetic radiation to thereby produce a desired wavelength of the electromagnetic radiation.

4. An optical computing device as defined in any of paragraphs 1-3, wherein the first and second polarizers comprise an actuation device to thereby manipulate an angular orientation of the first or second polarizers; and the wavelength scanner and the first and second polarizers are communicably coupled together to achieve systematic tuning to the desired wavelength and angular orientations to thereby mimic the regression vector.

5. An optical computing device as defined in any of paragraphs 1-4, wherein the first and second polarizers have different angular orientations.

6. An optical computing device as defined in any of paragraphs 1-5, wherein the angular orientation of the first polarizer defines a first polarization state of the sample-interacted light; and the angular orientation of the second polarizer defines a second polarization state of the first polarized light representing an intensity modulation between the first and second polarization states, wherein the intensity modulation is utilized to determine the characteristic of the sample.

7. An optical computing device as defined in any of paragraphs 1-6, wherein the first and second polarization states are any one of a pure P polarized light, pure S polarized light, or intermediate P and S polarized light.

8. An optical computing device as defined in any of paragraphs 1-7, further comprising an actuation device operatively coupled to at least one of the first or second polarizers to thereby manipulate an angular orientation of the first or second polarizers.

9. An optical computing device as defined in any of paragraphs 1-8, wherein: the first polarizer is operatively coupled to the actuation device; and the second polarizer is stationary.

10. An optical computing device as defined in any of paragraphs 1-9, wherein the first polarizer is fixed; and the second polarizer is operatively coupled to the actuation device.

11. An optical computing device as defined in any of paragraphs 1-10, further comprising a wavelength dispersive element positioned to optically interact with the sample-interacted light to thereby produce a dispersed sample-interacted light, wherein the first polarizer is a first array of polarizers positioned to optically interact with the dispersed sample-interacted light to thereby produce dispersed first polarized light; and the second polarizer is a second array of polarizers positioned to optically interact with the dispersed first polarized light to thereby produce dispersed second polarized light, each polarizer in the second array of polarizers having a corresponding polarizer in the first array of polarizers, thus forming a pair.

12. An optical computing device as defined in any of paragraphs 1-11, wherein each pair comprises different angular orientations.

13. An optical computing device as defined in any of paragraphs 1-12, wherein: each polarizer in the first array of polarizers has the same polarization; and the polarizers in the second array of polarizers have different polarizations that span a wavelength spectrum of the sample-interacted light to thereby modulate intensities of the dispersed first polarized light.

14. An optical computing device as defined in any of paragraphs 1-13, further comprising a lens positioned to optically interact with the dispersed second polarized light to thereby focus the dispersed second polarized light to the detector.

15. An optical computing device as defined in any of paragraphs 1-14, further comprising a signal processor communicably coupled to the detector to computationally determine the characteristic of the sample in real-time.

16. An optical computing device as defined in any of paragraphs 1-15, wherein the optical computing device comprises part of a downhole reservoir interrogation system.

17. An optical computing method to determine a characteristic of a sample, the method comprising optically interacting electromagnetic radiation with a sample to produce sample-interacted light; optically interacting the sample-interacted light with a first polarizer to produce first polarized light; optically interacting the first polarized light with a second polarizer to produce second polarized light; generating a signal that corresponds to the second polarized light through utilization of a detector; and determining a characteristic of the sample using the signal.

18. An optical computing method as defined in paragraph 17, wherein producing the second polarized light comprises weighting at least one orthogonal component of the sample-interacted light using a combined spectroscopic intensity profile of the first and second polarizers, the at least one orthogonal component corresponding to the characteristic of the sample.

19. An optical computing method as defined in paragraphs 17 or 18, further comprising optically interacting the electromagnetic radiation with a wavelength scanner to thereby produce a desired wavelength of the electromagnetic radiation, wherein the desired wavelength of the electromagnetic radiation optically interacts with the sample to produce the sample-interacted light.

20. An optical computing method as defined in any of paragraphs 17-19, further comprising tuning to the desired wavelength and polarizer angular orientations to thereby weight the at least one orthogonal component of the sample interacted light.

21. An optical computing method as defined in any of paragraphs 17-20, further comprising positioning the first and second polarizers at different angular orientations in relation to one another.

22. An optical computing method as defined in any of paragraphs 17-21, wherein: optically interacting the sample-interacted light with the first polarizer comprises defining a first polarization state of the sample-interacted light; and optically interacting the first polarized light with the second polarizer comprises defining a second polarization state of the first polarized light representing an intensity modulation between the first and second polarization states, wherein the intensity modulation is utilized to determine the characteristic of the sample.

23. An optical computing method as defined in any of paragraphs 17-22, further comprising dynamically manipulating an angular orientation of the first or second polarizers.

24. An optical computing method as defined in any of paragraphs 17-23, further comprising rotating at least one of the first or second polarizers to an angular orientation; and generating at least one of a pure P polarized light, pure S polarized light, or an intermediate P and S polarized light.

25. An optical computing method as defined in any of paragraphs 17-24, further comprising adjusting an angular orientation of the second polarizer to thereby modulate an intensity of the first polarized light.

26. An optical computing method as defined in any of paragraphs 17-25, further comprising optically interacting the sample-interacted light with a wavelength dispersive element to thereby produce a dispersed sample-interacted light, wherein optically interacting the sample-interacted light with the first polarizer comprises optically interacting the dispersed sample-interacted light with a first array of polarizers positioned to thereby produce dispersed first polarized light; and optically interacting the first polarized light with the second polarizer comprises optically interacting the dispersed first polarized light with a second array of polarizers to thereby produce dispersed second polarized light, each polarizer in the second array of polarizers having a corresponding polarizer in the first array of polarizers, thus forming a pair.

27. An optical computing method as defined in any of paragraphs 17-26, further comprising adjusting an angular orientation of the pairs such that a weighting of at least one orthogonal component of the sample-interacted light is achieved at a desired wavelength.

28. An optical computing method as defined in any of paragraphs 17-27, wherein: optically interacting the dispersed sample-interacted light with the first array of polarizers produces dispersed first polarized light having the same polarization states; and optically interacting the dispersed first polarized light with the second array of polarizers produces dispersed second polarized light have different polarization states that span a wavelength spectrum of the sample-interacted light, thereby modulating intensities of the dispersed first polarized light.

29. An optical computing method as defined in any of paragraphs 17-28, further comprising optically interacting the dispersed second polarized light with a lens to thereby focus the dispersed second polarized light to the detector.

30. An optical computing method as defined in any of paragraphs 17-29, wherein the method is performed in a downhole environment.

31. An optical computing device to determine a characteristic of a sample, the optical computing device comprising electromagnetic radiation having a first polarized state; a polarizer positioned to optically interact with the electromagnetic radiation to thereby produce a polarized light having a second polarized state, the polarized state optically interacting with a sample to produce sample-interacted light; and a detector positioned to measure the sample-interacted light and thereby generate a signal utilized to determine a characteristic of the sample.

32. An optical computing device as defined in paragraph 31, further comprising a tunable laser that produces the electromagnetic radiation, wherein the electromagnetic radiation further comprises a desired intensity and wavelength.

33. An optical computing device as defined in paragraphs 32 or 33, wherein a combined spectroscopic intensity profile of the tunable laser and the polarizer weights at least one orthogonal component of the sample-interacted light, the at least one orthogonal component corresponding to the characteristic of the sample.

34. An optical computing device as defined in any of paragraphs 31-33, wherein the polarizer comprises an actuation device to manipulate an angular orientation of the polarizer; and the tunable laser and the polarizer is communicably coupled together to achieve systematic tuning to the desired wavelength and angular orientation to weight the at least one orthogonal component of the sample-interacted light.

35. An optical computing device as defined in any of paragraphs 31-34, wherein an angular orientation of the polarizer defines the second polarization state of the polarized light, the second polarization state representing an intensity modulation between the first and second polarization states, wherein the intensity modulation is utilized to determine the characteristic of the sample.

36. An optical computing device as defined in any of paragraphs 31-35, wherein the first and second polarization states are any one of a pure P polarized light, pure S polarized light, or intermediate P and S polarized light.

37. An optical computing device as defined in any of paragraphs 31-36, further comprising a signal processor communicably coupled to the detector to computationally determine the characteristic of the sample in real-time.

38. An optical computing device as defined in any of paragraphs 31-37, wherein the optical computing device comprises part of a downhole reservoir interrogation system.

39. An optical computing method to determine a characteristic of a sample, the method comprising optically interacting electromagnetic radiation with a polarizer to produce polarized light, the electromagnetic radiation having a first polarization state and the polarized light having a second polarization state; optically interacting the polarized light with a sample to produce sample-interacted light; generating a signal that corresponds to the sample-interacted light through utilization of a detector; and determining a characteristic of the sample using the signal.

40. An optical computing method as defined in paragraph 39, wherein producing the polarized light comprises weighting at least one orthogonal component of the sample-interacted light using a combined spectroscopic intensity profile of the tunable laser and polarizer, the at least one orthogonal component corresponding to the characteristic of the sample.

41. An optical computing method as defined in paragraphs 39 or 40, wherein weighting the at least one orthogonal component of the sample-interacted light comprises selecting a wavelength and intensity for the electromagnetic radiation; and manipulating an angular orientation of the polarizer based upon the selected wavelength and intensity.

42. An optical computing method as defined in any of paragraphs 39-41, further comprising manipulating an angular orientation of the polarizer; and generating at least one of a pure P polarized light, pure S polarized light, or an intermediate P and S polarized light.

43. An optical computing method as defined in any of paragraphs 39-42, wherein the method is performed in a downhole environment.

44. An optical computing method to determine a characteristic of a sample, the method comprising optically interacting electromagnetic radiation with a sample to produce sample-interacted light; modulating an intensity of the sample-interacted light using at least one polarizer to thereby generate a polarized light; generating a signal that corresponds to the polarized light through utilization of a detector; and determining a characteristic of the sample using the signal.

45. An optical computing method as defined in paragraph 44, wherein modulating the intensity of the sample-interacted light comprises utilizing two polarizers to generate the polarized light.

46. An optical computing method as defined in paragraphs 44 or 45, wherein modulating the intensity of the sample-interacted light comprises manipulating an angular orientation of the at least one polarizer.

Although various embodiments and methodologies have been shown and described, the disclosure is not limited to such embodiments and methodologies, and will be understood to include all modifications and variations as would be apparent to one ordinarily skilled in the art. Therefore, it should be understood that the disclosure is not intended to be limited to the particular forms disclosed. Rather, the intention is to cover all modifications, equivalents and alternatives falling within the spirit and scope of the disclosure as defined by the appended claims.

What is claimed is:

1. An optical computing device to determine a characteristic of a sample, the optical computing device comprising:
electromagnetic radiation that optically interacts with a sample to produce sample-interacted light;

a first polarizer positioned to optically interact with the sample-interacted light to produce first polarized light;

a second polarizer positioned to optically interact with the first polarized light to produce second polarized light, wherein a combined spectroscopic intensity profile of the first and second polarizers mimics a multivariate regression vector that corresponds to as characteristic of the sample; and a detector positioned to measure the second polarized light and thereby generate a signal utilized to determine a presence of the characteristic in the sample.

2. The optical computing device as defined in claim 1, wherein the combined spectroscopic intensity profile of the first and second polarizers weights at least one orthogonal component of the sample-interacted light, the at least one orthogonal component corresponding to the characteristic of the sample.

3. The optical computing device as defined in claim 2, further comprising:

a broadband light source that produces the electromagnetic radiation; and a wavelength scanner positioned to optically interact with the electromagnetic radiation to thereby produce a desired wavelength of the electromagnetic radiation.

4. The optical computing device as defined in claim 3, wherein:

the first and second polarizers comprise an actuation device to thereby manipulate an angular orientation of the first or second polarizers; and the wavelength scanner and the first and second polarizers are communicably coupled together to achieve systematic tuning to the desired wavelength and angular orientations to thereby mimic the regression vector.

5. The optical computing device as defined in claim 1, wherein the first and second polarizers have different angular orientations.

6. The optical computing device as defined in claim 5, wherein:

the angular orientation of the first polarizer defines a first polarization state of the sample-interacted light; and the angular orientation of the second polarizer defines a second polarization state of the first polarized light representing an intensity modulation between the first and second polarization states, wherein the intensity modulation is utilized to determine the characteristic of the sample.

7. The optical computing device as defined in claim 6, wherein the first and second polarization states are any one of a pure P polarized light, pure S polarized light, or intermediate P and S polarized light.

8. The optical computing device as defined in claim 1, further comprising an actuation device operatively coupled to at least one of the first or second polarizers to thereby manipulate an angular orientation of the first or second polarizers.

9. The optical computing device as defined in claim 8, wherein:

the first polarizer is operatively coupled to the actuation device; and the second polarizer is stationary.

10. The optical computing device as defined in claim 8, wherein:

the first polarizer is fixed; and the second polarizer is operatively coupled to the actuation device.

11. The optical computing device as defined in claim 1, further comprising a wavelength dispersive element positioned to optically interact with the sample-interacted light to thereby produce a dispersed sample-interacted light, wherein:

the first polarizer is a first array of polarizers positioned to optically interact with the dispersed sample-interacted light to thereby produce dispersed first polarized light; and the second polarizer is a second array of polarizers positioned to optically interact with the dispersed first polarized light to thereby produce dispersed second polarized light, each polarizer in the second array of polarizers having a corresponding polarizer in the first array of polarizers, thus forming a pair.

12. The optical computing device as defined in claim 11, wherein each pair comprises different angular orientations.

13. The optical computing device as defined in claim 11, wherein:

each polarizer in the first array of polarizers has the same polarization; and the polarizers in the second array of polarizers have different polarizations that span a wavelength spectrum of the sample-interacted light to thereby modulate intensities of the dispersed first polarized light.

14. The optical computing device as defined in claim 13, further comprising a lens positioned to optically interact with the dispersed second polarized light to thereby focus the dispersed second polarized light to the detector.

15. The optical computing device as defined in claim 1, further comprising a signal processor communicably coupled to the detector to computationally determine the characteristic of the sample in real-time.

16. The optical computing device as defined in claim 1, wherein the optical computing device comprises part of a downhole reservoir interrogation system.

17. An optical computing method to determine a characteristic of a sample, the method comprising:

optically interacting electromagnetic radiation with a sample to produce sample-interacted light;

optically interacting the sample-interacted light with a first polarizer to produce first polarized light;

optically interacting the first polarized light with a second polarizer to produce second polarized light, wherein a combined spectroscopic intensity profile of the first and second polarizers minks a multivariate regression vector that corresponds to a characteristic of the sample;

generating a signal that corresponds to the second polarized light through utilization of a detector; and determining a presence of the characteristic in the sample using the signal.

18. The optical computing method as defined in claim 17, wherein producing the second polarized light comprises weighting at least one orthogonal component of the sample-interacted light using the combined spectroscopic intensity profile of the first and second polarizers, the at least one orthogonal component corresponding to the characteristic of the sample.

19. The optical computing method as defined in claim 18, further comprising optically interacting the electromagnetic radiation with a wavelength scanner to thereby produce a desired wavelength of the electromagnetic radiation, wherein the desired wavelength of the electromagnetic radiation optically interacts with the sample to produce the sample-interacted light.

20. The optical computing method as defined in claim 19, further comprising tuning to the desired wavelength and polarizer angular orientations to thereby weight the at least one orthogonal component of the sample interacted light.

21. The optical computing method as defined in claim 17, further comprising positioning the first and second polarizers at different angular orientations in relation to one another.

22. The optical computing method as defined in claim 21, wherein:
    optically interacting the sample-interacted light with the first polarizer comprises defining a first polarization state of the sample-interacted light; and
    optically interacting the first polarized light with the second polarizer comprises defining a second polarization state of the first polarized light representing an intensity modulation between the first and second polarization states, wherein the intensity modulation is utilized to determine the characteristic of the sample.

23. The optical computing method as defined in claim 17, further comprising dynamically manipulating an angular orientation of the first or second polarizers.

24. The optical computing method as defined in claim 23, further comprising:
    rotating at least one of the first or second polarizers to an angular orientation; and
    generating at least one of a pure P polarized light, pure S polarized light, or an intermediate P and S polarized light.

25. The optical computing method as defined in claim 17, further comprising adjusting an angular orientation of the second polarizer to thereby modulate an intensity of the first polarized light.

26. The optical computing method as defined in claim 17, further comprising optically interacting the sample-interacted light with a wavelength dispersive element to thereby produce a dispersed sample-interacted light, wherein:
    optically interacting the sample-interacted light with the first polarizer comprises optically interacting the dispersed sample-interacted light with a first array of polarizers positioned to thereby produce dispersed first polarized light; and
    optically interacting the first polarized light with the second polarizer comprises optically interacting the dispersed first polarized light with a second array of polarizers to thereby produce dispersed second polarized light, each polarizer in the second array of polarizers having a corresponding polarizer in the first array of polarizers, thus forming a pair.

27. The optical computing method as defined in claim 26, further comprising adjusting an angular orientation of the pairs such that a weighting of at least one orthogonal component of the sample-interacted light is achieved at a desired wavelength.

28. The optical computing method as defined in claim 26, wherein:
    optically interacting the dispersed sample-interacted light with the first array of polarizers produces dispersed first polarized light having the same polarization states; and
    optically interacting the dispersed first polarized light with the second array of polarizers produces dispersed second polarized light have different polarization states that span a wavelength spectrum of the sample-interacted light, thereby modulating intensities of the dispersed first polarized light.

29. The optical computing method as defined in claim 28, further comprising optically interacting the dispersed second polarized light with a lens to thereby focus the dispersed second polarized light to the detector.

30. The optical computing method as defined in claim 17, wherein the method is performed in a downhole environment.

31. An optical computing device to determine a characteristic of a sample, the optical computing device comprising:
    electromagnetic radiation having a first polarized state;
    a polarizer positioned to optically interact with the electromagnetic radiation to thereby produce a polarized light having a second polarized state, the polarized light optically interacting with a sample to produce sample-interacted light,
    wherein a spectroscopic intensity profile of the polarizer is used to mimic a multivariate regression vector that corresponds to a characteristic of the sample; and
    a detector positioned to measure the sample-interacted light and thereby generate a signal utilized to determine a presence of the characteristic in the sample.

32. The optical computing device as defined in claim 31, further comprising a tunable laser that produces the electromagnetic radiation, wherein the electromagnetic radiation further comprises a desired intensity and wavelength.

33. The optical computing device as defined in claim 32, wherein a combined spectroscopic intensity profile of the tunable laser and the polarizer weights at least one orthogonal component of the sample-interacted light, the at least one orthogonal component corresponding to the characteristic of the sample.

34. The optical computing device as defined in claim 33, wherein:
    the polarizer comprises an actuation device to manipulate an angular orientation of the polarizer; and
    the tunable laser and the polarizer is communicably coupled together to achieve systematic tuning to the desired wavelength and angular orientation to weight the at least one orthogonal component of the sample-interacted light.

35. The optical computing device as defined in claim 31, wherein an angular orientation of the polarizer defines the second polarization state of the polarized light, the second polarization state representing an intensity modulation between the first and second polarization states, wherein the intensity modulation is utilized to determine the characteristic of the sample.

36. The optical computing device as defined in claim 31, wherein the first and second polarization states are any one of a pure P polarized light, pure S polarized light, or intermediate P and S polarized light.

37. The optical computing device as defined in claim 31, further comprising a signal processor communicably coupled to the detector to computationally determine the characteristic of the sample in real-time.

38. The optical computing device as defined in claim 31, wherein the optical computing device comprises part of a downhole reservoir interrogation system.

39. An optical computing method to determine a characteristic of a sample, the method comprising:
    optically interacting electromagnetic radiation with a polarizer to produce polarized light, the electromagnetic radiation having a first polarization state and the polarized light having a second polarization state,
    wherein a spectroscopic intensity profile of the polarizer is used to mimic a multivariate regression vector that corresponds to a characteristic of the sample;
    optically interacting the polarized light with a sample to produce sample-interacted light;

generating a signal that corresponds to the sample-interacted light through utilization of a detector; and determining a presence of the characteristic in the sample using the signal.

40. An optical computing method as defined in claim 39, wherein producing the polarized light comprises weighting at least one orthogonal component of the sample-interacted light using a combined spectroscopic intensity profile of a tunable laser and polarizer, the at least one orthogonal component corresponding to the characteristic of the sample.

41. The optical computing method as defined in claim 40, wherein weighting the at least one orthogonal component of the sample-interacted light comprises:

selecting a wavelength and intensity for the electromagnetic radiation; and manipulating an angular orientation of the polarizer based upon the selected wavelength and intensity.

42. The optical computing method as defined in claim 39, further comprising:

manipulating an angular orientation of the polarizer; and generating at least one of a pure P polarized light, pure S polarized light, or an intermediate P and S polarized light.

43. The optical computing method as defined in claim 39, wherein the method is performed in a downhole environment.

44. An optical computing method to determine a characteristic of a sample, the method comprising:

optically interacting electromagnetic radiation with a sample to produce sample-interacted light;

modulating an intensity of the sample-interacted light using at least one polarizer to thereby generate a polarized light, wherein a spectroscopic intensity profile of the at least one polarizer is used to mimic a multivariate regression vector that corresponds to a characteristic of the sample;

generating a signal that corresponds to the polarized light through utilization of a detector; and determining a presence of the characteristic in the sample using the signal.

45. The optical computing method as defined in claim 44, wherein modulating the intensity of the sample-interacted light comprises utilizing two polarizers to generate the polarized light.

46. The optical computing method as defined in claim 44, wherein modulating the intensity of the sample-interacted light comprises manipulating an angular orientation of the at least one polarizer.

* * * * *

UNITED STATES PATENT AND TRADEMARK OFFICE
CERTIFICATE OF CORRECTION

| | | |
|---|---|---|
| PATENT NO. | : 9,599,554 B2 | Page 1 of 1 |
| APPLICATION NO. | : 14/423382 | |
| DATED | : March 21, 2017 | |
| INVENTOR(S) | : James M. Price and David L. Perkins | |

It is certified that error appears in the above-identified patent and that said Letters Patent is hereby corrected as shown below:

In the Claims

In Column 17, Line 7: please replace "as" with --a--;
In Column 18, Line 45: please replace "minks" with --mimics--.

Signed and Sealed this
Thirtieth Day of May, 2017

Michelle K. Lee
*Director of the United States Patent and Trademark Office*